United States Patent

Brocchini et al.

[11] Patent Number: 5,861,400
[45] Date of Patent: Jan. 19, 1999

[54] PHARMACEUTICAL COMPOUNDS

[75] Inventors: Stephen James Brocchini, Highland Park, N.J.; Justin Stephen Bryans, Slough, Great Britain; Christopher John Latham, Slough, Great Britain; Adrian John Folkes, Slough, Great Britain

[73] Assignee: Xenova Limited, United Kingdom

[21] Appl. No.: 693,169

[22] PCT Filed: Feb. 14, 1995

[86] PCT No.: PCT/GB95/00301

§ 371 Date: Nov. 4, 1996

§ 102(e) Date: Nov. 4, 1996

[87] PCT Pub. No.: WO95/21831

PCT Pub. Date: Aug. 17, 1995

[30] Foreign Application Priority Data

Feb. 14, 1994 [GB] United Kingdom ................ 9402805.7

[51] Int. Cl.[6] ...................... A61K 31/495; C07D 401/06; C07D 403/06; C07D 405/06
[52] U.S. Cl. .......................... 514/252; 514/253; 514/255; 544/360; 544/364; 544/372; 544/373; 544/379; 544/385; 544/405; 544/408
[58] Field of Search ..................................... 544/373, 360, 544/372, 379, 385, 405; 514/253, 252, 255

[56] References Cited

PUBLICATIONS

Chemical Abstracts, vol. 109, No. 3, 1988, Columbus, Ohio, U.S.; abstract No.16593a, Toshio Yokoi et al,.
Chemical Abstracts, vol. 69, No. 28, 1968, Columbus, Ohio, US; abstract No. 96654q, R.F.C. Brown.
Bellamy et al, *Cancer Investigation* 8(5), pp. 547–562 (1990).
Yokoi et al, *J. of Antiobiotics* vol. XLI, No. 4 pp. 494–501 (1988).
Wu et al, *Chemical Abstracts*, vol. 113, No. 17408p (1990).
Kamel et al, *J. of Antibiotics* vol. XLIII, No. 8, pp. 1018–1020 (1990).

*Primary Examiner*—Emily Bernhardt
*Attorney, Agent, or Firm*—Nixon & Vanderhye

[57] ABSTRACT

Piperazine derivatives of the formula

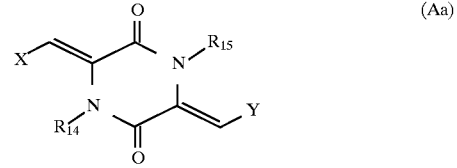

(Aa)

their esters and salts are useful as modulators of multiple drug resistance.

16 Claims, No Drawings

PHARMACEUTICAL COMPOUNDS

The present invention relates to compounds useful as modulators of multiple drug resistance (MDR), to their preparation and to pharmaceutical and veterinary compositions containing them.

The resistance of tumours to treatment with certain cytotoxic agents is an obstacle to the successful chemotherapeutic treatment of cancer patients. A tumour may acquire resistance to a cytotoxic agent used in a previous treatment. A tumour may also manifest intrinsic resistance, or cross-resistance, to a cytotoxic agent to which it has not previously been exposed, that agent being unrelated by structure or mechanism of act on to any agent used in previous treatments of the tumour.

Analogously, certain pathogens may acquire resistance to pharmaceutical agents used in previous treatments of the diseases or disorders to which those pathogens give rise. Pathogens may also manifest intrinsic resistance, or cross resistance, to pharmaceutical agents to which they have not previously been exposed. Examples of this effect include multi-drug resistant forms of malaria, tuberculosis, leishmaniasis and amoebic dysentery.

The above phenomena are referred to collectively as multi-drug resistance (MDR). As discussed more fully later on, a plasma membrane glycoprotein (P-gp) is implicated in the mechanism which underlies MDR. P-gp has drug binding properties. Certain agents which have the capacity to modulate MDR may therefore also be useful in facilitating the delivery of drugs across the blood-brain barrier and in treating AIDS and AIDS-related complex.

Disadvantages of drugs which have so far been used to modulate MDR, termed resistance modifying agents or RMAs, are that they frequently possess a poor pharmacokinetic profile and/or are toxic at the concentrations required for MDR modulation.

It has now been found that a series of diketopiperazine derivatives have activity as modulators of multiple drug resistance. The present invention therefore provides a piperazine of general formula (A):

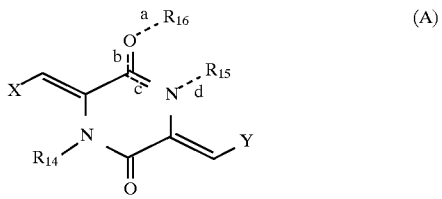

(A)

wherein denotes an optional bond, provided that both $\overset{a}{----}$ and $\overset{c}{----}$ are bonds and $\overset{b}{----}$ and $\overset{d}{----}$ are not bonds, or both $\overset{b}{----}$ and $\overset{d}{----}$ are bonds and $\overset{a}{----}$ and $\overset{c}{----}$ are not bonds;

X and Y, which may be the same or different, are independently selected from
 (i) a heterocyclic ring selected from furan, thiophene, pyridine and indole, the indole ring being optionally N-substituted by phthalimidyl-$C_1$–$C_6$-alkyl, succinimidyl-$C_1$–$C_6$-alkyl, oxo- or dioxo-indolenyl, —$(CH_2)_n COOR_{11}$, or —$(CH_2)_n COOCH_2Ph$, wherein $R_{11}$ is H or $C_1$–$C_6$ alkyl and n is 0, 1 or 2;
 (ii) a phenyl ring which is unsubstituted or substituted by one or more substituents selected from halogen, $C_1$–$C_6$ alkoxy, —$NO_2$ and $NR_{11}R_{12}$ wherein $R_{11}$ and $R_{12}$ are each, independently, H or $C_1$–$C_6$ alkyl;
 (iii) a cyclohexyl group; and
 (iv) a group —CH=C($R_{17}$)(Ar);
$R_{17}$ is H or optionally substituted phenyl and Ar is optionally substituted phenyl, the optional substituents on the phenyl ring in each case being selected from halogen, —$NO_2$, —$N(R_{11}R_{12})$ wherein $R_{11}$ and $R_{12}$ are as defined above and $C_1$–$C_6$ alkoxy;
$R_{14}$ is H or $C_1$–$C_6$ alkyl optionally substituted by phenyl;
$R_{15}$ is H or $C_1$–$C_6$ alkyl, optionally substituted by an N-phthalimidyl, N-succinimidyl or oxo- or dioxo-indolenyl group and
$R_{16}$ is $C_1$–$C_6$ alkyl optionally substituted by an N-phthalimidyl, N-succinimidyl or oxo- or dioxo-indolenyl group;

with the proviso that
 (a) X and Y are not both a phenyl ring as defined above under (ii), and
 (b) when $\overset{b}{----}$ and $\overset{d}{----}$ are both bonds at least one of $R_{14}$ and $R_{15}$ is other than hydrogen;

or a pharmaceutically acceptable salt or ester thereof.

In one embodiment the piperazine is of the following formula (Aa):

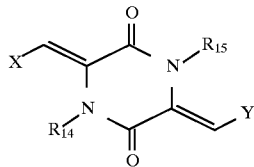

(Aa)

wherein $R_{14}$, $R_{15}$, X and Y are as defined above.

In another embodiment the piperazine is of the following formula (Ab):

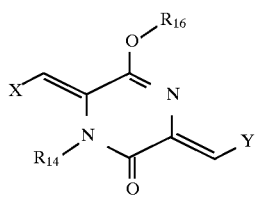

(Ab)

wherein $R_{14}$, $R_{16}$, X and Y are as defined above.

When either X or Y is a substituted phenyl ring, the benzene ring may be substituted at any of the ortho, meta and para positions by one or more substituents, for example one, two or three substituents, which may be the same or different, independently selected from the groups specified under (ii) above.

An alkyl group may be linear or branched, or may comprise a cycloalkyl group. A $C_1$–$C_6$ alkyl group is typically a $C_1$–$C_4$ alkyl group, for example a methyl, ethyl, propyl, i-propyl, n-butyl, sec-butyl, tert-butyl or cyclopropylmethyl group. A halogen is, for example, fluorine, chlorine, bromine or iodine. A $C_1$–$C_6$ alkyl group substituted by halogen may be substituted by 1, 2 or 3 halogen atoms. It may be a perhaloalkyl group, for example trifluoromethyl.

A $C_1$–$C_6$ alkoxy group is typically a $C_1$–$C_4$ alkoxy group, for example a methoxy, ethoxy, propoxy, i-propoxy, n-butoxy, sec-butoxy or tert-butoxy group.

In compounds of formula A free rotation may occur at room temperature about the single bonds connecting X and Y to the double bonds at positions 3 and 6 of the 2,5-piperazinedione ring. When either of X and Y is a phenyl group, therefore, positions 2 and 6, and positions 3 and 5, in both benzene rings can therefore be considered as equivalent.

When $$\underset{b}{----}$$

and $$\underset{d}{----}$$

are bonds in formula A at least one of $R_{14}$ and $R_{15}$ is other than hydrogen. When $R_{14}$ and $R_{15}$ are both $C_1$–$C_6$ alkyl they may be the same or different. Preferred $C_1$–$C_6$ alkyl groups for $R_{14}$ and $R_{15}$ are Me, Et and cyclopropylmethyl. For example $R_{14}$ is $C_1$–$C_6$ alkyl and $R_{15}$ is H or $C_1$–$C_6$ alkyl, or $R_{15}$ is $C_1$–$C_6$ alkyl and $R_{14}$ is H or $C_1$–$C_6$ alkyl. In one embodiment $R_{14}$ is Me, Et or cyclopropylmethyl and $R_{15}$ is H, Me, Et or cyclopropylmethyl. In a second embodiment $R_{15}$ is Me, Et or cyclopropylmethyl and $R_{14}$ is H, Me, Et or cyclopropylmethyl.

When $$\underset{a}{----}$$

and $$\underset{c}{----}$$

are both bonds in formula A, $R_{16}$ is $C_1$–$C_6$ alkyl optionally substituted by an N-phthalimidyl group and $R_{14}$ is H or $C_1$–$C_6$ alkyl, optionally substituted by phenyl. Typically $R_{14}$ or H is Me, Et or cyclopropylmethyl.

When X or Y is a phenyl ring it may be unsubstituted or mono-substituted at any one of positions 2 to 6 in the benzene ring. The benzene ring may instead be 2,3-, 2,4-, 2,5-, 2,6-, 3,4- or 3,5- disubstituted, or 2,3,4-, 2,3,5-, 2,3,6- or 3,4,5-trisubstituted.

In one embodiment one of X and Y is an unsubstituted or substituted phenyl ring and the other is a heterocyclic ring, a cyclohexyl group or a group —CH=CHPh or —CH=CH(Ph)$_2$. Preferred examples of a heterocyclic ring include a 4-pyridyl, furan-2-yl, furan-3-yl, thiophen-2-yl and optionally substituted indol-3-yl group.

In another embodiment $R_{16}$ is a phthalimidyl-$C_1$–$C_6$ alkyl group and Y is an optionally N-substituted indole ring.

In a third embodiment $R_{14}$ is $C_1$–$C_6$ alkyl substituted by phenyl and Y is a pyridine ring.

Certain diketopiperazines have been disclosed as having utility as bioactive agents. Yokoi et al in J. Antibiotics vol XLI No. 4, pp 494–501 (1988) describe structure-cytotoxicity relationship studies on a series of diketopiperazines related to neihumicin, a compound obtained from the micro-organism *Micromonospora neihuensis*. Kamei et al in J. Antibiotics vol XLIII No. 8, 1018–1020 disclose that two diketopiperazines, designated piperafizines A and B, have utility as potentiators of the cytotoxicity of vincristine.

Examples of specific compounds of the invention are as follows. The compound numbering is adhered to in the rest of the specification:

1894 (3Z,6Z)-6-Benzylidene-1-methyl-3-(1-tert-butoxycarbonyl-3-(1-tert-butoxycarbonyl-3-indolyl)methylene-2,5-piperazinedione.

1895 (3Z,6Z)-6-Benzylidene-1-methyl-5-(3-phthalimidopropoxy)-3-(1-tert-butoxycarbonyl-3-indolyl)methylene-3,6-dihydro-2-pyrazinone.

1899 (37)-1-Acetyl-3-benzylidene-5-(3-phthalimidopropoxy)-1,2,3,6-tetrahydro-2-pyrazinone.

1855 (3Z,6Z)-3,6-Dibenzylidene-1-methyl-5-pentyloxy-3,6-dihydro-2-pyrazinone.

1840 (3Z,6Z)-1-Benzyl-6-benzylidene-3-(4-pyridyl)methylene-2,5-hydrochloride.

1834 (3Z,6Z)-1,4-Dimethyl-3-(1-tert-butoxycarbonyl-3-indolyl)methylene-6-(2-thenylidene)-2,5-piperazinedione.

1839 (3Z,6Z)-1-Benzyl-6-benzylidene-3-(4-pyridyl)methylene-2,5-piperazinedione.

1932 (3Z,6Z)-3,6-Dibenzylidene-4-methyl-1-(3-succinimidopropyl)-2,5-piperazinedione.

1934 (3Z,6Z)-3,6-Dibenzylidene-1-methyl-5-(3-succinmidopropoxy)-3,6-dihydro-2-pyrazinone.

1942 (3Z,6Z)-3-Benzylidene-1,4-dimethyl-6-(1-tert-butoxycarbonyl)-3-indolyl)methylene-2,5-piperazinedione.

1943 (3Z,6Z)-3-Benzylidene-1,4-dimethyl-6-(3-(1-(3-phthalimido)propyl)indolyl)methylene-2,5-piperazinedione.

1941 (3Z,6Z)-3-Benzylidene-6-1-methoxycarbonyl-3-indolyl)methylene-1,4-dimethyl-2,5-piperazinedione.

1940 (3Z,6Z)-3-Benzylidene-6-(1-benzyloxycarbonyl-3-indolyl)methylene-1,4-dimethyl-2,5-piperazinedione.

1935 (3Z,6Z)-3,6-Dibenzylidene-5-(2,3-dioxo-1-indolinyl) propoxy-1-methyl-3,6-dihydro-2-pyrazinone.

1937 (3Z,6Z)-3-Benzylidene-1,4-dimethyl-6-(γ-phenylcinnamylidene)-2,5-piperazinedione.

1800 (3Z,6Z)-3-Benzylidene-1,4-dimethyl-6-(1-tert-butoxycarbonyl-3-indolyl)methylene-2,5-piperazinedione.

1947 (3Z,6Z)-3,6-Di-(3-(2-dimethylaminoethoxy)benzylidene)-2,5-piperazinedione.

1596 (3Z,6Z)-6-(3-furylmethylene)-3-(4-methoxybenzylidene-1-methyl-2,5-piperazinedione.

1938 (3Z,6Z)-3-Benzylidene-6-(4-dimethylaminobenzylidene)-1,4-dimethyl-2,5-piperazinedione.

1933 (3Z,6Z)-6-Benzylidene-3-cyclohexylmethylene-1-methyl-2,5-piperazinedione.

1799 (3Z,6Z)-3-Benzylidene-6-(2-furyl)-1,4-dimethyl-2,5-piperazinedione.

1896 (3Z,6Z)-3-Benzylidene-6-(3-indoly)methylene-1,4-dimethyl-2,5-piperazinedione.

1597 (3Z,6Z)-3-(4-Methoxybenzylidene)-1-methyl-6-(2-thienylmethylene)-2,5-piperazinedione.

1641 (3Z,6Z)-3-Benzylidene-1-methyl-6-(3-thienylmethylene)-2,5-piperazinedione.

1771 (3Z,6Z)-3,6-Dibenzylidene-5-methoxy-1-methyl-3,6-dihydro-2-pyrazinone.

1570 (3Z,6Z)-6-Benzylidene-5-methoxy-3-(2-thenylidene)-3,6-dihydro-2(1H)-pyrazinone.

1563 (3Z,6Z)-3-(3-Furyl)methylene-6-(4-methoxybenzylidene)-1-methyl-2,5-piperazinedione.

1565 (3Z,6Z)-6-(4-Methoxybenzylidene)-1-methyl-3-(1-tert-butoxycarbonyl-3-indolyl)methylene-2,5-piperazinedione.

1777 (3Z,6Z)-3-Cinnamylidene-6-(4-methoxybenzylidene)-1,4-dimethyl-2,5-piperazinedione.

1836 (3Z,6Z)-6-Benzylidene-3-furylidene-1,4-dimethyl-2,5-piperazinedione.

1871 (3Z,6Z)-3-Benzylidene-6-cyclohexylmethylene-1,4-dimethyl-2,5-piperazinedione.

1873 (3Z,6Z)-6-(2,6-dichlorobenzylidene)-3-(1-tertbutoxycarbonyl-3-indolyl)methylene-1,4-dimethyl-2,5-piperazinedione.

1874 (3Z,6Z)-4-benzyl-3-(1-tertbutoxycarbonyl-3-indolyl)methylene-6-(4-methoxybenzylidene)-1-methyl-2,5-piperazinedione.

1875 (3Z,6Z)-6-(3-furylmethylene)-6-(1-tertbutoxycarbonyl-3-indolyl)methylene-1,4-dimethyl-2,5-piperazinedione.

1877 (3Z,6Z)-1,4-dimethyl-6-(2-nitrobenzylidene)-3-(2-thienylmethylene)-2,5-piperazinedione.

1880 (3Z,6Z)-4-Benzyl-3-(3-furylmethylene)-6-(4-methoxybenzylidene)-1-methyl-2,5-piperazinedione.

1563 (3Z,6Z)-3-(3-Furylmethylene)-6-(4-methoxybenzylidene)-1-methyl-2,5-piperazinedione.

1564 (3Z,6Z)-6-(4-Methoxybenzylidene)-1-methyl-3-(2-thienylmethylene)-2,5-piperazinedione.

1569 (3Z,6Z)-3-Benzylidene-1-methyl-6-(2-thienylmethylene)-2,5-piperazinedione.

Compounds of formula A may be prepared by a process which comprises either (a) condensing a compound of formula (I):

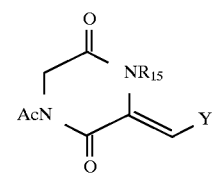

wherein $R_{15}$ and Y are as defined above and are optionally protected, with a compound of formula (II):

wherein X is as defined above and is optionally protected, in the presence of a base in an organic solvent, thereby obtaining a compound of formula A in which $R_{14}$ is hydrogen; or (ii) condensing a compound of formula (I'):

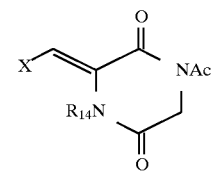

wherein $R_{14}$ and X are as defined above and are optionally protected, with a compound of formula (III):

wherein Y is as defined above and is optionally protected, in the presence of a base in an organic solvent, thereby obtaining a compound of formula A in which $R_{15}$ is hydrogen; and, in either case (i) or (ii), if desired, converting the resulting compound of formula A in which $R_{14}$ or $R_{15}$, respectively, is hydrogen into a corresponding compound of formula A in which $R_{14}$ and $R_{15}$, respectively, is a $C_1$–$C_6$ alkyl group, by treatment with an alkylating agent of formula $R_{14}$—X or $R_{15}$—X wherein $R_{14}$ and $R_{15}$ are as defined above and X is halogen; or, if desired, converting a compound of formula A in which $R_{15}$ is hydrogen into a compound of formula A wherein $R_{16}$ is as defined above, by treatment with an alkylating agent of formula $R_{16}$—X wherein $R_{16}$ is as defined above and X is a halogen, and/or if required, removing optionally present protecting groups and/or, if desired, converting one compound of formula A into another compound of formula A, and/or, if desired, converting a compound of formula A into a pharmaceutically acceptable salt or ester thereof, and/or, if desired, converting a salt or ester into a free compound, and/or, if desired, separating a mixture of isomers of compounds of formula A into the single isomers.

The process can give rise to a mixture of O-alkylated and N-alkylated products, i.e. a mixture of compounds of formula (Aa) and (Ab), as defined above, wherein $R_{15}$ and $R_{16}$ are the same. The relative proportions of the two products will vary depending on the nature of $R_{15}$ and $R_{16}$, which determines in turn the relative extent of N-alkylation compared to O-alkylation. The two may be separated by conventional methods, for example column chromatography, and obtained separately.

A compound of formula A produced directly by the condensation reaction between (I) and (II) or (I') and (III) may be modified, if desired, by converting optional substituents on groups X and Y into other substituents. These optional conversions may be carried out by methods known in themselves. For example, a compound of formula A in which X or Y is an indolyl group may be converted into a compound of formula A wherein the imidazoyl group is N-substituted by treatment with an appropriately substituted halide such as benzyl haloformate, a haloalkylphthalimide or an alkylhaloacetate, for instance in DMSO at room temperature.

A compound of formula A in which one of X and Y is a phenyl group substituted by an $NO_2$ group may be converted into a compound of formula A in which one of X and Y is a phenyl group substituted by an amino group $N(R_{11}R_{12})$ by reduction under standard conditions, for example by catalytic hydrogenation.

Protecting groups for substituents on X or Y in any of the compounds of formulae (I), (I'), (II) and (III) are optionally introduced prior to step (i) or step (ii) when any of those substituents are groups which are sensitive to the condensation reaction conditions or incompatible with the condensation reaction, for example an amino group. The protecting groups are then removed at the end of the process. Any conventional protecting group suitable for the group in question may be employed, and may be introduced and subsequently removed by well-known standard methods.

The condensation reaction between compounds (I) and (II) or (I') and (III) is suitably performed in the presence of a base which is potassium t-butoxide, sodium hydride, potassium carbonate, sodium carbonate, caesium carbonate, sodium acetate, potassium fluoride on alumina, or triethylamine in a solvent such as dimethylformamide, or in the presence of potassium t-butoxide in t-butanol or a mixture of t-butanol and dimethylformamide. The reaction is typically performed at a temperature from 0° C. to the reflux temperature of the solvent.

The alkylation of a compound of formula A wherein $R_{14}$ or $R_{15}$ is H is carried out using an appropriate conventional alkylating agent such as a haloalkane, for example an iodoalkane, or a dialkylsulphate, in the presence of a base in an organic solvent. The base may be, for example, sodium hydride, sodium carbonate or potassium carbonate. A suitable solvent is then DMF. Another suitable base is aqueous sodium hydroxide, in which case a suitable cosolvent is, for example, dioxan, THF or DMF.

The compounds of formula (I) may be prepared by a process comprising reacting 1,4-diacetyl-2,5-piperazinedione with a compound of formula (III) as defined above, in the presence of a base in an organic solvent, thereby obtaining a compound of formula (I) wherein $R_{15}$ is hydrogen; and, if desired, treating the resulting compound of formula (I) with an alkylating agent to obtain a compound of formula (I) in which $R_{15}$ is a $C_1$–$C_6$ alkyl group. Similarly, the compounds of formula (I') may be prepared by a process which comprises reacting 1,4-diacetyl-2,5-piperazinedione with a compound of formula (II) as defined above, in the presence of a base in an organic solvent, thereby obtaining a compound of formula (I') in which $R_{14}$ is hydrogen; and, if desired, treating the resulting compound of formula (I') with an alkylating agent to obtain a compound of formula (I') in which $R_{14}$ is a $C_1$–$C_6$ alkyl group.

If necessary, the resulting compound of formula (I) or (I') can be separated from other reaction products by chromatography.

The reaction of 1,4-diacetyl-2,5-piperazinedione with the compound of formula (III) or (II) is suitably performed under the same conditions as described above for the condensation between compounds (I) and (II), or (I') and (III).

The alkylation of a compound of formula (I) in which $R_{15}$ is hydrogen, or a compound of formula (I') in which $R_{14}$ is hydrogen, is suitably carried out using the same conventional alkylating agents and under the same conditions as described above for the alkylation of compounds of formula (A) in which $R_{14}$ is hydrogen. The alkylation step in the case of a compound (I) where $R_{15}$ is hydrogen typically gives rise to a mixture of the compound of formula (I) in which $R_{15}$ is a $C_1$–$C_6$ alkyl group and its isomer of the following formula (IV) in which $R_{15}$ is a $C_1$–$C_6$ alkyl group:

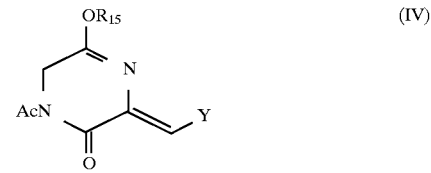

The alkylation step in the case of a compound (I') where $R_{14}$ is hydrogen typically gives rise to a mixture of the compound of formula (I') where $R_{14}$ is a $C_1$–$C_6$ alkyl group and its isomer of formula (IV') where $R_{14}$ is a $C_1$–$C_6$ alkyl group:

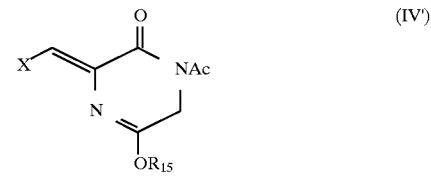

The mixture of compounds (I) and (IV), where $R_{15}$ is other than hydrogen, or compounds (I') and (IV'), where $R_{14}$ is other than hydrogen, can readily be separated by chromatography, for example on silica gel. Suitable eluants include ethyl acetate and hexane, or methanol and dichloromethane.

The substituted benzaldehydes of formulae (II) and (III) are known compounds or can be prepared from readily available starting materials by conventional methods. The 1,4-diacetyl-2,5-piperazinedione used as a starting material in the preparation of compounds of formula (I) may be prepared by treating 2,5-piperazinedione (glycine anhydride) with an acetylating agent. The acetylation may be performed using any conventional acetylating agent, for example acetic anhydride under reflux or, alternatively, acetic anhydride at a temperature below reflux in the presence of 4-dimethylaminopyridine.

Compounds of formula (I) wherein $R_{15}$ is H may also be prepared by the microwave irradiation of a mixture comprising 1,4-diacetyl-2,5-piperazinedione, a compound of formula (III) and potassium fluoride on alumina (as base) in the absence of solvent.

Compounds of formula (I) wherein $R_{15}$ is H may alternatively be prepared directly from 2,5-piperazinedione (glycine anhydride) by a process which comprises treating the 2,5-piperazinedione with a mixture comprising a compound of formula (III), sodium acetate and acetic anhydride at an elevated temperature, for example under reflux.

Compounds of formula (I') wherein $R_{14}$ is H may be prepared by analogous processes, replacing compound (III) in each case by a compound of formula (II).

Compounds of formula A may also be prepared by a process comprising the microwave irradiation of (i) a mixture comprising a compound of formula (I) as defined above wherein $R_{15}$ is H or $C_1$–$C_6$ alkyl, a compound of formula (II) and potassium fluoride on alumina, or (ii) a mixture comprising a compound of formula (I') wherein $R_{14}$ is H or $C_1$–$C_6$ alkyl a compound of formula (III) and potassium fluoride on alumina, or (iii) a mixture comprising 1,4- diacetylpiperazine-2,5-dione, a compound of formula (II), a compound of formula (III) and potassium fluoride on alumina. The irradiation is performed in the absence of a solvent. The resulting compound in which $R_{14}$ and $R_{15}$ are both H may then be alkylated using an appropriate alkylating agent, for example as described above.

Compounds of formula A may also be obtained directly by a process which comprises condensing together 1,4-diacetyl-2,5-piperazinedione, a compound of formula (II) and a compound of formula (III) in the presence of a base in an organic solvent. Suitable bases, solvents and reaction conditions are as described above for the condensation reaction between, for example, compounds (I) and (II).

An alternative direct process for the preparation of compounds of formula A comprises condensing together 2,5-piperazinedione, a compound of formula (II) and a compound of formula (III) in the presence of sodium acetate and acetic anhydride at elevated temperature, for example under reflux.

An alternative process for the preparation of compounds of formula (I) comprises treating a compound of formula (V):

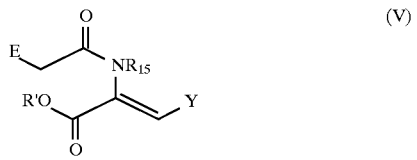

wherein $R_6$ to $R_{10}$ are as defined above, X is a halogen and R' is a $C_1$-$C_6$ alkyl group, with ammonia followed by acetic anhydride.

Compounds of formula (I') may be prepared by an analogous process which comprises treating a compound of formula (V'):

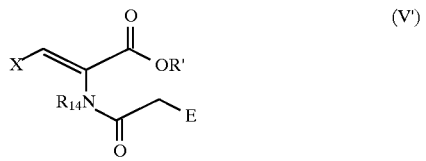

wherein $R_1$ to $R_5$, X and R' are as defined above, with ammonia followed by acetic anhydride.

X in formula (V) or (V') is typically iodine. R' is, for example, a $C_1$-$C_4$ alkyl group such as a methyl, ethyl, propyl, i-propyl, butyl, sec-butyl or tert-butyl group.

A review of synthetic approaches to unsaturated 3-monosubstituted and 3,6-disubstituted-2,5-piperazinediones is provided in Heterocycles, 1983, 20, 1407 (C.Shin).

Compounds of formula (A) may be converted into pharmaceutically acceptable salts, and salts may be converted into the free compound, by conventional methods. Suitable salts include salts with pharmaceutically acceptable, inorganic or organic, bases, or pharmaceutically acceptable inorganic or organic acids. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, triethylamine, benzylamine, dibenzylamine or α- or β-phenylethylamine, and heterocyclic bases such as piperidine, 1-methylpiperidine and morpholine. Examples of inorganic acids include hydrochloric acid, sulphuric acid and orthophosphoric acid. Examples of organic acids include p-toluenesulphonic acid, methanesulphonic acid, mucic acid and butan-1,4-dioic acid.

Compounds of formula (A) may also be converted into pharmaceutically acceptable esters. Suitable esters include branched or unbranched, saturated or unsaturated $C_1$-$C_6$ alkyl esters, for example methyl, ethyl and vinyl esters.

Cancer cells which exhibit multiple drug resistance, referred to as MDR cells, display a reduction in intracellular drug accumulation compared with the corresponding drug-sensitive cells. Studies using in vitro derived MDR cell lines have shown that MDR is often associated with increased expression of a plasma membrane glycoprotein (P-gp) which has drug binding properties. P-gp is thought to function as an efflux pump for many hydrophobic compounds, and transfection studies using cloned P-gp have shown that its overexpression can confer the MDR phenotype on cells: see, for example, Ann. Rev. Biochem 58 137–171 (1989).

A major function of P-gp in normal tissues is to export intracellular toxins from the cell. There is evidence to suggest that overexpression of P-gp may play a clinical role in multiple drug resistance. Increased levels of P-gp mRNA or protein have been detected in many forms of human cancers—leukaemias, lymphomas, sarcomas and carcinomas. Indeed, in some cases P-gp levels have been found to increase in tumour biopsies obtained after relapse from chemotherapy.

Inhibition of P-gp function in P-gp mediated MDR has been shown to lead to a net accumulation of anti-cancer agent in the cells. For example, Verapamil a known calcium channel blocker was shown to sensitise MDR cells to vinca alkaloids in vitro and in vivo: Cancer Res., 41, 1967–1972 (1981). The proposed mechanism of action involves competition with the anti-cancer agent for binding to the P-gp. A range of structurally unrelated resistance-modifying agents acting by this mechanism have been described such as tamoxifen (Nolvadex:ICI) and related compounds, and cyclosporin A and derivatives.

Compounds of formula A and their pharmaceutically acceptable salts and esters (hereinafter referred to as "the present compounds") have been found in biological tests to have activity in modulating multiple drug resistance. The results are set out in Example 10 which follows. The present compounds may therefore be used as multiple drug resistance modifying agents, also termed resistance-modifying agents, or RMAs. The present compounds can modulate, e.g. reduce, or eliminate multiple drug resistance. The present compounds can therefore be used in a method of potentiating the cytotoxicity of an agent which is cytotoxic to a tumour cell. Such a method comprises, for instance, administering one of the present compounds to the tumour cell whilst the tumour cell is exposed to the cytotoxic agent in question. The therapeutic effect of a chemotherapeutic, or antineoplastic, agent may thus be enhanced. The multiple drug resistance of a tumour cell to a cytotoxic agent during chemotherapy may be reduced or eliminated.

The present compounds can also be used in a method of treating a disease in which the pathogen concerned exhibits multi-drug resistance, for instance multi-drug resistant forms of malaria (Plasmodium falciarum), tuberculosis, leishmaniasis and amoebic dysentery. Such a method comprises, for instance, administering one of the present compounds with (separately, simultaneously or sequentially) the drug to which the pathogen concerned exhibits multi-drug resistance. The therapeutic effect of the drug may thus be enhanced.

A human or animal patient harbouring a tumour may be treated for resistance to a chemotherapeutic agent by a method comprising the administration thereto of one of the present compounds. The present compound is administered in an amount effective to potentiate the cytotoxicity of the said chemotherapeutic agent. Examples of chemotherapeutic or antineoplastic agents which are preferred in the context of the present invention include vinca alkaloids such as vincristine and vinblastine; anthracycline antibiotics such as daunorubicin and doxorubicin; mitoxantrone; actinomycin D and plicamycin.

In addition, a human or animal patient suffering from a disease in which the responsible pathogen exhibits multi-drug resistance may be treated for resistance to a therapeutic agent by a method comprising the administration thereto of one of the present compounds.

Examples of such disease include multi-drug resistant forms of malaria (*Plasmodium falciparum*), tuberculosis, leishmaniasis and amoebic dysentery.

MDR modulators also have utility in the delivery of drugs across the blood-brain barrier, and in the treatment of AIDS and AIDS-related complex. The present compounds can therefore be used in a method of facilitating the delivery of drugs across the blood brain barrier, and in the treatment of AIDS or AIDS-related complex. A human or animal patient in need of such treatment may be treated by a method comprising the administration thereto of one of the present compounds.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 10 mg/kg, most commonly in the range of 0.01 to 5 mg/kg, body weight. Such a dosage may be given, for example, from 1 to 5 times daily by bolus infusion, infusion over several hours and/or repeated administration.

A piperazine of formula (A) or a pharmaceutically acceptable salt or ester thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as a modulator of multiple drug resistance comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. A compound may be encapsulated within liposomes.

The following Examples illustrate the invention:

REFERENCE EXAMPLE 1

Preparation of (3Z,6Z)-6-Benzylidene-3-(4-methoxybenzylidene)-2,5-5 piperazinedione (3)

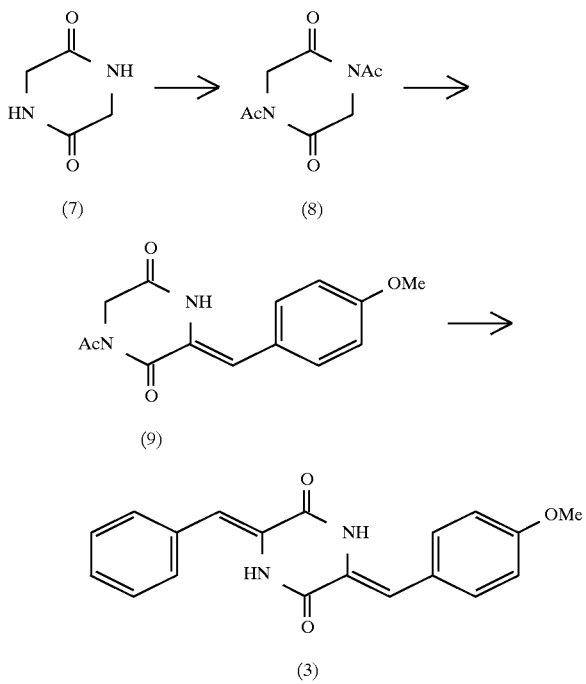

1,4-Diacetyl-2,5-piperazinedione (8)

1,4-Diacetyl-2,5-piperazinedione (8) was prepared by the published procedure (S. M. Marcuccio and J. A. Elix, *Aust. J. Chem.,* 1984, 37, 1791).

(3z)-1-Acetyl-3-(4-methoxybenzylidene)-2,5-piperazinedione (9)

(3Z)-1-Acetyl-3-(4-methoxybenzylidene)-2,5-piperazinedione (9) was prepared by the published procedure (T. Yokoi, LM. Yang, T. Yokoi, RY. Wu, and KH. Lee, *J. Antibiot.,* 1988, 41, 494).

(3Z,6Z)-6-Benzylidene-3-(4-methoxybenzylidene)-2,5-piperazinedione (3)

A mixture of (3Z)-1-acetyl-3-(4-methoxybenzylidene)-2,5-piperazinedione (9) (1.0 g, 3.6 mmol), benzaldehyde (430 μl, 4.2 mmol) and triethylamine (1.14 ml), 8.2 mmol), in dry DMF (20 ml), was heated at 130° C. for 18 h. The reaction mixture was cooled to room temperature and poured into ethyl acetate (100 ml). A yellow solid precipitated which was filtered off and dried. Yield 360 mg (31%).

$C_{19}H_{16}N_2O_3$

¹H nmr (400 MHz d₆-DMSO)
δ: 3.80 (3H, s, O—Me); 6.77 (1H, s, CH=C); 6.78 (1H, s, CH=C); 6.98 (2H, d, J=8 Hz, 2×C—H on Ar—OMe); 7.30–7.56 (7H, m, Ph and 2×C—H on Ar—OMe); 10.15 (2H, br.s, N—H).
¹³C nmr (100 MHz d₆-DMSO)
δ: 58.68; 117.66; 118.03; 118.77; 128.11; 128.92; 129.95; 131.53; 132.11; 132.69; 134.44; 136.59; 161.39; 161.62; 162.71.
ms (desorption chemical ionisation, ammonia):
m/z (% relative intensity) : 321 (100) MH⁺.
ir : KBr (diffuse reflectance):
ν max (cm⁻¹) : 1620, 1700, 3100, 3220.
Elemental analysis:
Calculated for $C_{19}H_{16}N_2O_3$: C 71.24, H 5.03, N 8.74.
Found: C 70.92, H 5.02, N 8.80. C 70.89, H 5.06, N 8.79%

REFERENCE EXAMPLE 2

Preparation of (3Z,6Z)-6-Benzylidene-3-(4-methoxybenzylidene)-2,5-piperazinedione (3)

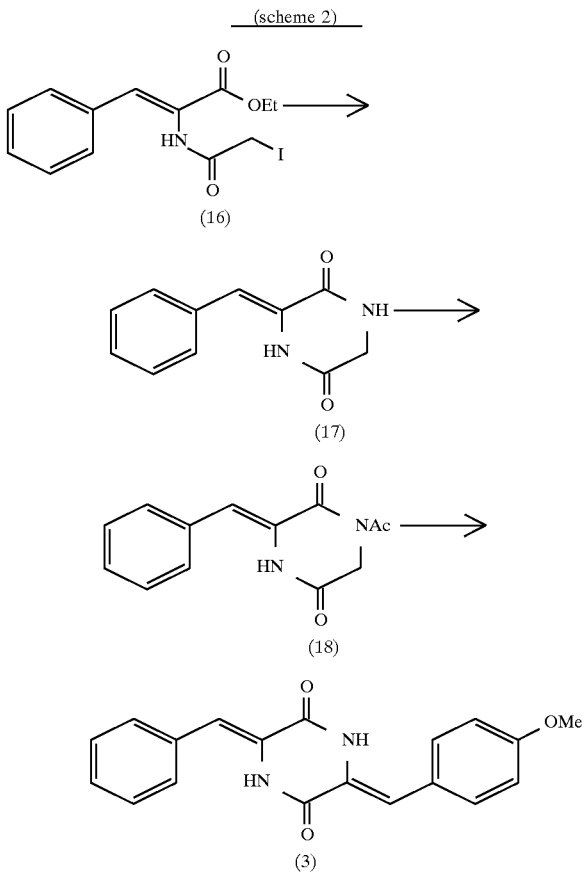

Compound 16 is treated with ammonia and subsequently with acetic anhydride to yield 1-acetyl-3-benzylidene-2,5-piperazinedione (18).

Compound 18 is then condensed, in the presence of caesium carbonate or triethylamine in DMF, with 4-methoxybenzaldehyde to yield compound 3.

REFERENCE EXAMPLE 3

Preparation of 1-acetyl-3-benzylidene-2,5-piperazinedione 1,4-Diacetyl-2,5-piperazinedione (25.0 g, 126 mmol), which is compound (8) mentioned in Reference Example 1, was heated at 120°–130° C. in DMF (200 ml) with triethylamine (17.6 ml, 126 mmol) and benzaldehyde (13.0 ml, 126 mmol). After 4 h the mixture was cooled to room temperature and poured into EtOAc (1000 ml), and washed three times with brine. Any solid formed at this stage was filtered off. The filtrate was dried (MgSO₄) and the solvent removed in vacuo. The residue was recrystallised from EtOAc:Hexane to give 11.78 g (38%) of the title compound as a yellow solid.

¹H NMR (CDCl₃ 400 MHz) δ=2.69 (3H, s) 4.54 (2H, s) 7.20 (1H, s) 7.40 (3H, m), 7.48 (2H, m), 7.93 (1H, br.s)
MS(DCI,NH₃): 262 (MNH₄⁺, 20%), 245 (MH⁺, 53%), 220 (52%), 204 (100%), 203 (100%)

| Microanalysis | C | H | N |
|---|---|---|---|
| Calc | 63.93 | 4.95 | 11.47 |
| Found | 64.11 | 5.02 | 11.41 |
|  | 64.05 | 4.90 | 11.44 |

REFERENCE EXAMPLE 4

Preparation of 1-acetyl-3-(4-acetamidobenzylidene)-2,5-piperazinedione 1,4-Diacetyl-2,5-piperazinedione (10.0 g, 50 mmol), prepared by the published procedure mentioned in Reference Example 1, was stirred in DMF (40 ml) with 4-acetamidobenzaldehyde (8.24 g, 50 mmol) and triethylamine (7 ml, 50 mmol) and heated to 120° C. After 2½ h the mixture was cooled to room temperature, diluted with EtOAc (100 ml) and stirred overnight. The solid formed was collected, washed with EtOAc and dried to give 8.46 g (56%) of a yellow solid.

¹H NMR (CDCl₃+CF₃CO₂H, 400 MHz) δ=2.32 (3H, s) 2.72 (3H, s) 4.68 (2H, s) 7.36 (1H, s) 7.45 (2H, d, J=8 Hz) 7.60 (2H, d, J=8 Hz)

| Microanalysis | C | H | N |
|---|---|---|---|
| Calc | 59.80 | 5.02 | 13.95 |
| Found | 60.08 | 5.09 | 13.89 |
|  | 60.11 | 5.07 | 13.86 |

REFERENCE EXAMPLE 5

Preparation of (3Z)-1-acetyl-3-(4-methoxybenzylidene)-2,5-piperazinedione (9) and 1-acetyl-3-(4-methoxybenzylidene)-4-methyl-2,5-piperazinedione (10)

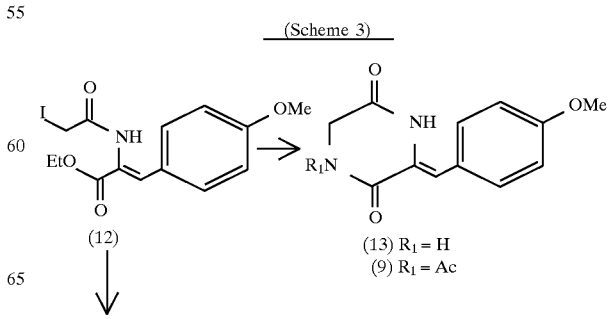

-continued
(Scheme 3)

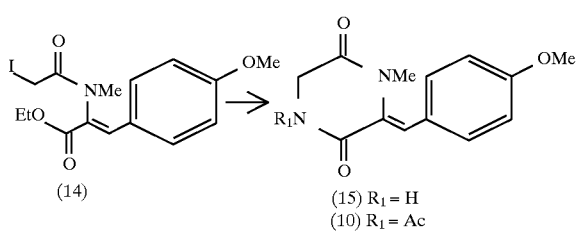

Compound 12 is treated with NH₃ to afford 3-(4-methoxybenzylidene-2,5-piperazinedione (13). This is then treated with acetic anhydride to yield (3Z)-1-acetyl-3-(4-methoxybenzylidene-2,5-piperazinedione (9).

Compound 12 is treated with, as methylating agent, iodomethane in the presence of potassium carbonate in dimethylformamide to give compound 14. Compound 14 is then treated with NH₃ and subsequently with acetic anhydride to yield 1-acetyl-3-(4-methoxybenzylidene)-4-methyl-2,5-piperazinedione (10).

REFERENCE EXAMPLE 6

Preparation of (3Z,6Z)-3-benzylidene-6-(4-methoxybenzylidene)-1-methyl-2,5-piperazine dione (1)

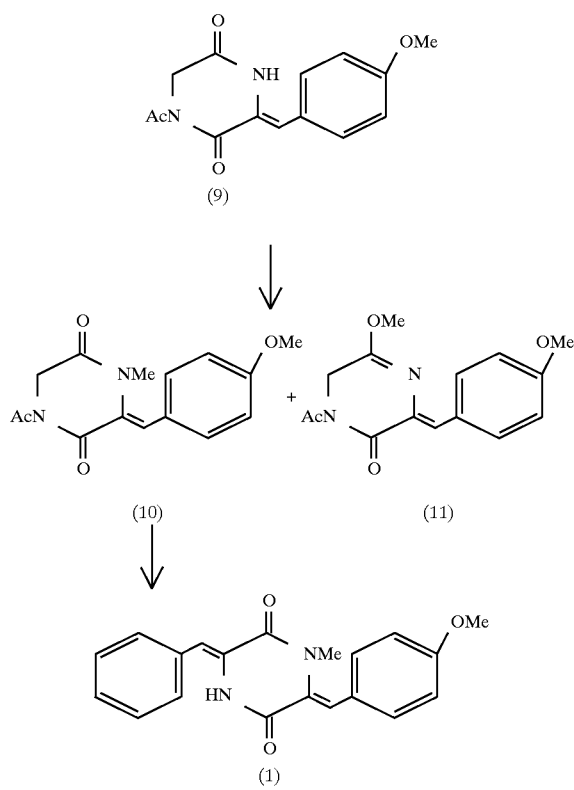

(3Z)-1-Acetyl-3-(4-methoxybenzylidene)-4-methyl-2,5-piperazinedione (10) and 1-Acetyl-5-methoxy-3-(4-methoxybenzylidene)-3,6-dihydropyrazin-2-one (11)

A mixture of (3Z)-1-Acetyl-3-(4-methoxybenzylidene)-2,5-piperazinedione (9) (2.0 g, 7.3 mmol), methyl iodide (0.46 ml, 7.3 mmol), and sodium carbonate (800 mg, 7.5 mmol) in dry DMF (50 ml) was stirred under an atmosphere of dry nitrogen for 3 days. The reaction mixture was then poured into ethyl acetate (500 ml) and washed with water (4×100 ml) and brine. The organic phase was separated, dried (MgSO₄), and the solvent removed in vacuo. The residue was purified by flash chromatography (silica, EtOAc:Hexane, 1:1) to give (3Z)-1-acetyl-3-(4-methoxybenzylidene)-4-methyl-2,5-piperazinedione (10) 1.38 g (66%) as a yellow solid and 1-acetyl-5-methoxy-3-(4-methoxybenzylidene)-3,6-dihydropyrazin-2-one (11) 248 mg (11.8%) as a bright yellow solid.

(3Z)-1-Acetyl-3-(4-methoxybenzylidene)-4-methyl-2,5-piperazinedione (10):
$C_{15}H_{16}N_2O_4$
¹H nmr (400 MHz CDCl₃):
  δ: 2.63 (3H, s, Ac); 2.95 (3H, s, N—Me); 3.87 (3H, s, O—Me); 4.52 (s, 2H, N—CH₂—CO); 6.93 (2H, d, J=8 Hz, Aromatic); 7.26 (1H, s, C=CH); 7.29 (2H, d, J=8 Hz), Aromatic).
ms (desorption chemical ionisation, ammonia):
m/z (% relative intensity): 306 (34%) MNH₄⁺; 289 (100%) 216 (14%)
ir : KBr (diffuse reflectance) ν $_{max}$ (cm⁻¹) : 1690, 1700, 3000.
Elemental analysis:
Calculated for $C_{15}H_{16}N_2O_4$: C 62.49, H 5.59, N 9.72 C 62.48, H 5.58, N 9.68. C 62.51, H 5.65, N 9.67%
1-Acetyl-5-methoxy-3-(4-methoxybenzylidene)-3,6-dihydropyrazin-2-one (11):
$C_{15}H_{16}N_2O_4$
¹H nmr (400 MHz CDCl₃)
  δ: 2.68 (3H, s, Ac); 3.86 (3H, s, Ar—OMe); 3.99 (3H, s, O—Me); 4.44 (s, 2H, N—CH₂—CO); 6.95 (2H, d, J=8 Hz, Ar); 7.32 (1H, s, C=CH); 8.03 (2H, d, J=8 Hz, Ar).
ms (desorption chemical ionisation, ammonia):
m/z (% relative intensity): 289 (100%) MH³⁰; 247 (14%)
ir : KBr (diffuse reflectance):
V $_{max}$ (cm⁻¹) : 1610, 1690, 1700, 1740, 2950.
Elemental Analysis:
Calculated for $C_{15}H_{16}N_2O_4$: C 62.49, H 5.59, N 9.72. C 62.52, H 5.59, N 9.64. C 62.52, H 5.64, N 9.66%
(3Z,6Z)-3-Benzylidene-6-(4-methoxybenzylidene)-1-methyl-2,5-piperazinedione (1)

A mixture of (3Z)-1-Acetyl-3-(4-methoxybenzylidene)-4-methyl-2,5 -piperazinedione (10) (200 mg, 0.69 mmol) and sodium hydride (60% dispersion in oil, 28 mg, 0.69 mmol) in dry DMF (10 ml) was stirred at room temperature for 18 h. Benzaldehyde (71 μl, 0.69 mmol) was then added and the reaction mixture stirred at room temperature for 18 h. It was then diluted with ethyl acetate (100 ml) and washed with brine (4×50 ml). The organic phase was separated, dried (MgSO₄), and the solvent removed in vacuo. The residue was purified by flash chromatography (silica, dichloromethane containing 1% MeOH) to give 48 mg (21 w) of a yellow solid.

$C_{20}H_{18}N_2O_3$
¹H nmr (400 MHz CDCl₃):
  δ: 3.06 (3H, s, N—Me); 3.87 (3H, s, O—Me); 6.93 (2H, d, J=8 Hz, 2×C—H on Ar—OMe); 7.06 (1H, s, Ph—CH=C); 7.23 (2H, d, J=8 Hz, 2×C—H on Ar—OMe); 7.27 (1H, s, MeOAr—CH=C); 7.30–7.48 (5H, m, Ph); (1H, br.s, N—H).
¹³C nmr (100 MHz CDCl₃)
  δ: 36.62; 55.34; 113.86; 116.80; 121.30; 126.02; 126.14; 128.47; 128.78; 129.06; 129.45; 131.11; 133.07; 159.66; 159.68; 159.95.
ms (desorption chemical ionisation, ammonia) : 335 (100%) MH⁺.

ir : KBr (diffuse reflectance) : v $_{max}$ (cm$^{-1}$) : 1690, 3000, 3180, 3400.
Elemental analysis:
Calculated for $C_{20}H_{18}H_2O_3$: O 71.84, H 5.43, N 8.38. C 71.81, H 5.31, N 8.31. C 71.80, H 5.25, N 8.31%.

REFERENCE EXAMPLE 7

Preparation of (3Z,6Z)-3-benzylidene-6-(4-methoxybenzylidene)-1,4-dimethyl-2,5-piperazinedione (2)

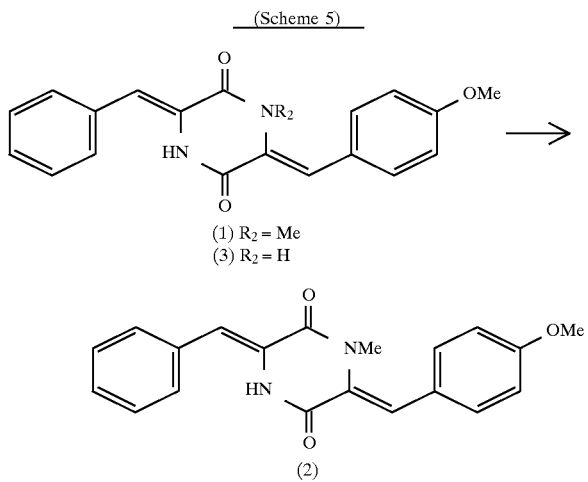

(3Z,6Z)-3-Benzylidene-6-(4-methoxybenzylidene)-1,4-dimethyl-2 5-piperazinedione (2)
A mixture of (3Z,6Z)-3-Benzylidene-6-(4-methoxybenzylidene)-2,5-piperazinedione (3) (0.5 g, 1.56 mmol), sodium hydride (60% dispersion in mineral oil, 125 mg, 3.1 mmol) and methyl iodide (243 μl, 3.9 mmol) in dry DMF (50 ml) was stirred at room temperature for 4 days. The solvent was then removed in vacuo and the residue purified by flash chromatography (silica, eluting with EtOAc:Hexane, 1:3) to give 220 mg (40%) of compound 2 as a yellow solid.
$C_{21}H_{20}N_2O_3$
$^1$H nmr (400 MHz CDCl$_3$)
δ: 2.95 (3H, s, N—Me); 3.04 (3H, s, N—Me); 3.85 (3H, s, O—Me); 6.90 (2H, d, J=8 Hz, 2×C—H on Ar—OMe); 7.19 (1H, s, CH═C); 7.21 (1H, s, CH═C) 7.30–7.56 (7H, m, Ph and 2×C—H on Ar—OMe).
ms (desorption chemical ionisation, ammonia) :
m/z (% relative intensity): 349 (100) MH$^+$.

EXAMPLE 1

Preparation of 1894

1-acetyl-3-benzylidene-2,5-piperazinedione, prepared as described in Reference Example 3, was treated with the aldehyde formed by the reaction between indole-3-carboxaldehyde and di-tert-butyldicarbonate in acetonitrile in the presence of Et$_3$N (1 equivalent) and DMAP (0.1 equivalent) at room temperature for 72 hours; the reaction was performed in DMF in the presence of Cs$_2$CO$_3$ (1.1 equivalent) at 90° C. for 2 hours. The resulting compound was recrystallised from ethylacetate to give compound 1894 in 27% yield.

EXAMPLE 2

Preparation of 1896

Compound 1894 prepared as described in Example 1, was alkylated with methyl iodide (5 equivalents) in THF in the presence of sodium hydride (1.1 equivalent) at room temperature for 18 hours, to give compound 1800 in 88% yield.
Subsequent treatment of 1800 with excess TFA, in dichloromethane for 18 hours gave compound 1896 in 47% yield.

EXAMPLE 3

Preparation of Further Compounds of the Invention

Compound 1896, prepared as described in Example 2, was converted into further compounds of formula A using the following reagents and conditions:

(a) Treatment with sodium hydride (1.1 equivalent) and benzylchloroformate (3 equivalents) in DMSO at room temperature for 2 hours gave compound 1940 in 48% yield.

(b) Treatment of 1896 with bromomethylphthalimide (2 equivalents) and sodium hydride (1.1 equivalents) in THF with a few drops of DMF at room temperature for 72 hours gave compound 1897 in 72% yield.

(c) Treatment of 1896 with methyl bromoacetate (3 equivalents) and sodium hydride (1.1. equivalent) in DMSO at room temperature for 24 hours gave compound 1941 in 39% yield.

(d) Treatment of 1896 with t-butyl bromoacetate (3 equivalents) and sodium hydride (2 equivalents) in DMSO at room temperature for 18 hours gave compound 1942 in 18% yield.

(e) Treatment of 1896 with bromopropylphthalimide (3 equivalents) and sodium hydride (2 equivalents) in DMSO at 60° C. for 2 hours gave compound 1943 which was subsequently purified by column chromatography using SiO$_2$/20–40% EtOAc in hexane. Compound 1943 was obtained in 15% yield.

EXAMPLE 4

Preparation of 1895

Compound 1894, prepared as described in Example 1, was treated with 3-bromopropylphthalimide and sodium hydride (1.1. equivalents) in DMF at room temperature to give compound 1895 in 62% yield.

EXAMPLE 5

Preparation of 1938

1-acetyl-3-benzylidene-2,5-piperazinedione, prepared as described in Reference Example 3, was treated with 4-dimethylaminocinnamaldehyde and Cs$_2$CO$_3$ in DMF at 80° C. for 4 hours. The product of that reaction (1921) was treated first with sodium hydride in DMF for 10 minutes and then with methyliodide (3 equivalents) for 4 hours. The product was purified by column chromatography (silica, EtOAc/hexane) to yield 1938 in 25% yield.

EXAMPLE 6

Preparation of 1937

1-acetyl-3-benzylidene-2,5-piperazinedione, prepared as described in Reference Example 3, was treated with β-phenylcinnamaldehyde in DMF in the presence of Cs$_2$CO$_3$ at 80° C. The product of that reaction (1922) was recrystallised from acetic acid. It was then treated first with sodium hydride (2.5 equivalents) in DMF for 10 minutes, followed by iodomethane (3 equivalents) for 4 hours. The product was purified by column chromatography on silica to give 1937.

EXAMPLE 7

Preparation of 1933

1-acetyl-3-benzylidene-4-methyl-2,5-piperazinedione was treated with cyclohexanecarboxaldehyde (4 equivalents) in the presence of potassium t-butoxide (2 equivalents) in t-butanol and DMF at 100° C. for 90 minutes. The product was recrystallised from ethyl acetate/hexane to give compound 1933 in 29% yield.

EXAMPLE 8

Preparation of Further Compounds A

Further compounds of the invention may be prepared in accordance with the method described in Example 5 as follows. The starting material 1-acetyl-3-benzylidene-2,5-piperazinedione (a compound of general formula I in which Y is a phenyl ring) is replaced by the appropriate compound of formula (I) in which Y has the definition desired in the final product; this starting material may be prepared by reacting 1,4-diacetyl-2,5-piperazinedione, prepared as described in Reference Example 1, with the appropriate aldehyde Y—CHO.

The desired starting material of formula (I) thus produced is reacted with the appropriate substituted aldehyde (of formula X—CHO wherein X has the definition desired in the final product) and the remainder of the reaction is the performed as described in Example 5. The following compounds can be prepared in this manner: 1875, 1873, 1836, 1834, 1877, 1799, 1777 and 1871.

Similarly, the process described in Example 1 may be used to prepare other compounds of formula A in which $R_{14}$ is methyl and $R_{15}$ is hydrogen, by the use of appropriately substituted aldehydes Y—CHO and X—CHO. The following compounds may be prepared in this way: 1563, 1564, 1565, 1569, 1596, 1597 and 1641.

EXAMPLE 9

Pharmaceutical Composition

Tablets, each weighing 0.15 g and containing 25 mg of a compound of the invention can be manufactured as follows:
Composition for 10,000 tablets compound of the invention (250 g)

lactose (800 g)

corn starch (415 g)

talc powder (30 g)

magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 10

Testing of compounds A as modulators of MDR
Materials and Methods

The EMT6 mouse mammary carcinoma cell line and the MDR resistant subline AR 1.0 were cultured in RPMI 1640 medium containing 10% foetal calf serum and 2mM glutamine at 37° C. in 5% $CO_2$. Cells were passaged between 1 in 200 and 1 in 2000 in the case of the parental cell line and between 1 in 20 and 1 in 200 in the case of the MDR resistant subline, after trypsinisation (0.25% trypsin, 0.2 $gl^{-1}$, EDTA).

1. Drug accumulation assay

AR 1.0 cells were seeded into 96 well opaque culture plates (Canberra Packard). The assay medium contained a mixture of tritiated Daunorubicin (DNR), a cytotoxic agent, and unlabelled DNR (0.25$\mu$ Ci/ml; 2 $\mu$M). Compounds of formula A were serially diluted in assay medium over a range of concentrations from 100 nM to 100 $\mu$M. The cells were incubated at 37° C. for 1 hr before washing and counting of cell associated radioactivity. Each assay included a titration of the known resistance modifying agent Verapamil as positive control. Results were expressed as % maximum accumulation where 100% accumulation is that observed in the presence of 100 $\mu$M Verapamil.

The results are set out in the following Table 1.

| Compound No. | IC50 ($\mu$m) Accumulation | MAX accumulation (% 100 $\mu$m VRP) |
|---|---|---|
| 1563 | — | 32.9 |
| 1564 | — | 46.3 |
| 1565 | — | 37.3 |
| 1569 | — | 46.0 |
| 1596 | — | 47.7 |
| 1597 | 50.0 | 59.1 |
| 1641 | — | 50.5 |
| 1777 | 80.0 | 50.0 |
| 1799 | — | 40.0 |
| 1800 | 7.0 | — |
| 1834 | 5.0 | — |
| 1836 | — | 14.0 |
| 1839 | 20.0 | — |
| 1840 | 12.0 | — |
| 1871 | 6.0 | — |
| 1873 | 5.0 | 56.0 |
| 1874 | 10.0 | — |
| 1875 | 5.0 | — |
| 1877 | 20.0 | — |
| 1880 | 7.0 | — |
| 1894 | — | 36.0 |
| 1895 | — | 12.0 |
| 1896 | 12.0 | — |
| 1897 | 3.0 | — |
| 1940 | 10.0 | — |
| 1941 | 10.0 | — |
| 1942 | 10.0 | — |
| 1943 | 10.0 | — |
| 1932 | 10.0 | — |
| 1934 | 1.0 | — |
| 1935 | 6.0 | — |

2. Potentiation of Doxorubicin toxicity

Compounds of formula A were examined for their ability to potentiate the toxicity of doxorubicin in AR 1.0 cells. In initial proliferation assays compounds were titrated against a fixed concentration of doxorubicin (0.5–1 $\mu$M) which alone is non-toxic to AR 1.0 cells. Incubations with doxorubicin were over a four day period before quantitation of proliferation using the calorimetric sulphorhodamine B assay (Skehan et al; J. Natl. Cancer Inst. 82 pp 1107–1112 (1990)).

Compounds which were shown to be able to sensitise AR 1.0 cells to 0.8-1.7 $\mu$M doxorubicin without high innate toxicity were selected for further study. Cells were cultured for four days with concentrations of doxorubicin over the range of 0.5 nM–50 $\mu$M in the presence of Verapramil at its maximum subtoxic level determined from previous experiments. Proliferation was quantified as described by Skehan et al, loc cit. The $IC_{50}$ (concentration required to reduce proliferation to 50% of the untreated controls) for doxorubicin alone and with the Verapamil were derived and used to calculate the potentiation index (PI):

$$PI = \frac{IC_{50} \text{ for Doxorubicin alone}}{IC_{50} \text{ for Doxorubicin plus RMA}}$$

| Compound No. | Conc Comp μM | Potentiation Index (at 5 μM) |
|---|---|---|
| 1800 | 5 | 40 |
| 1834 | 3 | 30 (3 μm) |
| 1839 | 3 | 15 (3 μm) |
| 1871 | 5 | 20 |
| 1874 | 5 | 20 |
| 1897 | 5 | 75 |
| 1940 | 5 | 14 |
| 1941 | 5 | 4 |
| 1942 | 5 | 20 |
| 1943 | 5 | 20 |

TABLE 3

| COMPOUND NO. | CONC CYTOTOXIC AGENT (μg/ml) | COMPOUND TOXICITY (IC50 μM) | TOXICITY WITH CYTOTOXIC AGENT (IC 50 μM) |
|---|---|---|---|
| 1597 | 1.00 | 25.0 | 6.0 |
| 1641 | 1.00 | — | 0.0 |
| 1800 | 1.00 | 10.0 | 0.8 |
| 1834 | 0.50 | 10.0 | 0.8 |
| 1839 | 0.50 | 30.0 | 1.5 |
| 1840 | 0.50 | 5.0 | 1.0 |
| 1871 | 0.50 | 40.0 | 1.0 |
| 1873 | 0.50 | 8.0 | 0.8 |
| 1875 | 0.50 | 10.0 | 0.8 |
| 1880 | 0.50 | 10.0 | 1.0 |
| 1896 | 0.50 | 30.0 | 4.0 |
| 1897 | 0.50 | 50.0 | 1.5 |
| 1940 | 0.50 | 7.0 | 0.7 |
| 1941 | 0.50 | 50.0 | 1.5 |
| 1942 | 0.50 | 15.0 | 0.7 |
| 1943 | 0.50 | 60.0 | 0.2 |

EXAMPLE 11
Characterization of Compounds of Formula A

The compounds of Formula A were characterised by conventional mass spectorscopic, microanalytical, proton NMR and infra-red techniques. The results are set out in Table 4.

| No. | Mol. Formula (M. Wt) | Mass spec m/z, mass intensity (mode) | $^1$H nmr Solvent δ all 400 MHz | Microanalysis | | |
|---|---|---|---|---|---|---|
| | | | | | Calc | Found |
| XR1943 | $C_3H_{28}N_4O_4$ 544 | 545 57% MH+ 417 8% 358 13% 206 45% CI NH$_3$ | CDCl$_3$ 2.29(2H, p), 2.99(3H, s), 3.16(3H s), 3.78(2H, t), 4.25(2H, t), 7.21–7.41 (overlapping solvent & multiple sample signals), 7.43(1H, s), 7.68(1H, d), 7.73(2H, m), 7.86(2H, m) | | | |
| XR1942 | $C_{28}H_{29}O_4N_3$ 471 | 471 37% M+ 415 100% 357 26% 213 12% 168 28% 116 22% 89 8% EI+ | CDCl$_3$ 1.46(9H, s), 2.99(3H, s), 3.15(3H, s), 4.78(2H, s), 7.19–7.47 (overlapping solvent & multiple sample signals), 7.69(1H, d). | | | |
| XR1941 | $C_{25}H_{23}O_4N_3$ 429 | 430 100% MH+ CI NH$_3$ | CDCl$_3$ 3.00(3H, s), 3.15(3H, s), 3.79(3H, s), 4.90(2H, s), 7.19–7.45 (overlapping solvent and multiple sample signals). 7.72(1H, d) | | | |
| XR1940 | $C_{30}H_{25}N_3O_4$ 491 (491.547). | 492.59 15% MH+, 358.47 50%, 217.37 10% 169.23 27% CI NH$_3$ | CDCl$_3$ 3.0(3H, s), 3.08(3H, s), 5.50(2H, s), 7.25–7.48 | C H N | 73.31 5.13 8.55 | 73.03 5.16 8.46 | 73.06 5.17 8.41 |

23

-continued

| No. | Mol. Formula (M. Wt) | Mass spec m/z, mass intensity (mode) | $^1$H nmr Solvent δ all 400 MHz | Microanalysis | Calc | Found |
|---|---|---|---|---|---|---|
| | | | (overlapping solvent & sample peaks), 7.51(2H, d), 7.60(1H d), 7.65(1H, s), 8.21(1H, d). | | | |
| XR1897 | $C_{31}H_{24}O_4N_4$ 516 | 516 100% M+ 356 20% 160 100% 116 22% 77 15% EI+ | CDCl$_3$ 2.94(3H, s), 3.14(3H, s), 6.00(2H, s), 7.21–7.28 (overlapping solvent and sample peaks), 7.30–7.42(7H, c), 7.59(1H, s), 7.65(1H, d), 7.75(2H, m), 7.88(3H, c). | | | |
| XR1896 | $C_{22}H_{19}O_2N_3$ 357 | 357 100% M+ 155 34% 116 13% EI+ | CDCl$_3$ 2.99(3H, s), 3.12(3H, s), 7.20(multiple signals & solvent), 7.69(1H, d), 8.56(1H, br, s). | | | |
| XR1895 | $C_{37}H_{34}N_4O_6$ 630 | 630 1% M+ 530 20% 188 100% 160 39% 41 41% EI+ | CDCl$_3$ 1.67(9H, s), 2.33(2H, m), 2.98(3H, s), 3.98(2H, t), 4.59(2H, t), 6.82(1H, s), 7.19(1H, d), 7.27–7.39(7H, c), 7.53(3H, overlapping signals), 7.76(1H, m), 7.82(1H, d), 8.19(1H, d), 8.53(1H, s). | C H N | 70.46 5.43 8.88 | 69.90 5.47 8.98 | 69.77 5.48 8.93 |
| XR1894 | $C_{26}H_{25}$ | NO SPECTRUM OBSERVED CI NO SPECTRUM OBSERVED FAB+ 443 30% 387 18% 315 7% 132 28% 91 15% 57 100% EI+ | CDCl$_3$ 1.71(9H, s), 3.03(3H, s), 7.17(1H, s), 7.28(8H, c), 7.68(1H, d), 7.35 | C H N | 70.41 5.68 9.47 | 70.23 5.62 9.45 | 70.22 5.61 9.47 |
| XR1875 | $C_{25}H_{25}N_3O_5$ 447 | 448 100% DCI NH$_3$ | CDCl$_3$ 1.69(9H, s), 3.05(3H, s), 3.19(3H, s), 6.49(1H, s), 7.06(1H, s), 7.28–7.33 (overlapping solvent & sample signal), 7.38(1H, t), 7.49(1H, s), 7.54–7.61(3H, c), 8.16(1H, d). | | | |
| XR1873 | $C_{27}H_{25}N_3O_4Cl_2$ | 526 14% 469 18% 434 39% 426 100% | CDCl$_3$ 1.70(9H, s), 2.82(3H, s), 3.08(3H, s), 7.10(1H, s), 7.21–7.46 (overlapping solvent & sample signals), 7.57(1H, d), 7.65(1H, s), | C H N | 61.60 4.79 7.98 | 61.30 4.72 7.99 | 61.38 4.71 8.00 |

-continued

| No. | Mol. Formula (M. Wt) | Mass spec m/z, mass intensity (mode) | $^1$H nmr Solvent δ all 400 MHz | Microanalysis | Calc | Found |
|---|---|---|---|---|---|---|
| XR1836 | $C_{18}H_{16}N_2O_3$ 308 | MH+ 309 DCI NH$_3$ | 8.18(1H, d). CDCl$_3$ 7.58(1H, s), 7.48(1H, s), 7.35(H,), 7.20(2H, s), 7.05(1H, s), 6.45(1H, s), 3.18(3H, s), 2.95(3H, s). | C H N | | |
| XR1834 | $C_{25}H_{25}N_3O_4S$ 463 | 464 44% 402 81% 363 100% DCI NH$_3$ | CDCl$_3$ 1.69(9H, s), 3.06(3H, s), 3.20(3H, s), 7.09–7.13(2H, m), 7.28–7.32(2H, m), 7.39(1H, t), 7.46(1H, d), 7.57(1H, d), 7.60(1H, s), 8.17(1H, d). | C H N | 64.78 5.44 9.06 | 64.53 5.49 8.95 | 64.56 5.42 8.94 |
| XR1563 | $C_{18}H_{16}N_2O_4$ 324 | 325 100% DCI NH$_3$ | CDCl$_3$ 3.05(3H, s), 3.87(3H, s), 6.61(1H, broad s), 6.88(1H, s), 6.92(2H, d), 7.22–7.28 (overlapping solvent & sample signals), 7.55(1H, brs), 7.74(1H, s), 7.78(1H, V.brs). | C H N | 66.66 4.97 8.64 | 66.40 4.91 8.60 | 66.11 4.94 8.50 |
| XR1564 | $C_{18}H_{16}N_2O_3S$ 340 | 341 100% DCI NH$_3$ | CDCl$_3$ 3.06(3H, s), 3.85(3H, s), 6.91(2H, d), 7.13–7.30 (overlapping solvent & sample signals), 7.49(1H, d), 7.99(1H, V.brs). | C H N S | 63.51 4.74 8.23 9.42 | 63.39 4.73 8.19 9.31 | 63.36 4.74 8.16 9.42 |
| XR1565 | $C_{27}H_{27}N_3O_5$ 473 | 474 100% 374 80% DCI NH$_3$ | CDCl$_3$ 1.71(9H, s), 3.08(3H, s), 3.87(3H, s), 6.92(2H, d), 7.16(1H, s), 7.25–7.28 (overlapping solvent & sample signal), 7.35(1H, t), 7.41(1H, t), 7.69(1H, d), 7.86(1H, s), 8.01(1H, s), 8.19(1H, s). | C H N | 68.49 5.75 8.87 | 68.04 5.64 8.90 | 67.74 5.61 8.81 |
| XR1569 | $C_{17}H_{14}N_2O_2S$ MW = 310 | 328 (M+NH$_4$, 8%), 311 (MH+, 100%) DCI NH$_3$ | CDCl$_3$ 3.20(3H, s), 7.04–7.10(3H, m), 7.30(1H, s), 7.35–7.48(6H, m), 8.13(1H, brs). | | | |
| XR1596 | $C_{18}H_{16}O_4N_2$ 324 | 325 (100%) DCI NH$_3$ | CDCl$_3$ 3.21(3H, s), 3.85(3H, s), 6.45(1H, s), 6.95–7.01(3H, overlapping signals), 7.06(1H, s), 7.35(2H, d), 7.45(1H, fine m), 7.52(1H, brs), 7.90(1H, V.brs). | C H N | 66.66 4.97 8.64 | 66.61 4.90 8.56 | 66.71 4.97 8.57 |

-continued

| No. | Mol. Formula (M. Wt) | Mass spec m/z, mass intensity (mode) | $^1$H nmr Solvent δ all 400 MHz | Microanalysis | Calc | Found |
|---|---|---|---|---|---|---|
| XR1597 | $C_{18}H_{16}O_3N_2S$ 340 | 341 (100%) DCI $NH_3$ | CDCl$_3$ 3.19(3H, s), 3.85(3H, s), 6.95–7.10(5H, multiple signals), 7.29(1H, s), 7.36(2H, d), 7.43(1H, d), 7.94(1H, V.brs). | C H N S | 63.51 4.74 8.23 9.42 | 63.68 4.79 8.22 9.35 | 63.71 4.69 8.21 9.29 |
| XR1840 | $C_{24}H_{20}N_3O_2Cl$ | 417 (M+, 1%), 383 (34%), 382 (100%) DCI $NH_3$ | CDCl$_3$ 4.85(2H, s), 6.93(3H, m), 7.20(3H, m), 7.22–7.50(H, m), 8.00(2H, d, J=4Hz), 8.77(2H, d, J=4Hz), 10.52(1H, brs). | | | |
| XR1641 | $C_{17}H_{14}N_2O_2S$ MW = 310 | 328 (M$^+$NH$_4$, 4%) 311 (MH+, 100%) DCI $NH_3$ | CDCl$_3$ 3.10(3H, s), 7.07(1H, s), 7.08(1H, d), 7.20–7.48(8H, m), 7.94(1H, brs). | C H N | 65.79 4.55 9.03 | 65.72 4.53 9.02 | 65.77 4.53 9.02 |
| XR1839 | $C_{24}H_{19}N_3O_2$ | 382 (MH+, 100%). DCI $NH_3$ | CDCl$_3$ 4.85(2H, s), 6.89(2H, m), 6.95(1H, s), 7.20(3H, m), 7.22–7.50(8H, m), 7.91(1H, brs), 8.68(2H, d, J=5Hz) | | | |
| XR1874 | $C_{34}H_{33}N_3O_5$ 563 | 564 29% 507 25% 463 100% | CDCl$_3$ 1.71(9H, s), 3.00(3H, s), 3.83(3H, s), 4.82(2H, s), 6.90(2H, d), 7.00(2H, m), 7.15–7.22(4H, (multiple signals), 7.25–7.42 (overlapping solvent & sample signlas), 7.57(1H, d), 7.71(1H, s), 8.20(1H, d). | C H N | 72.45 5.90 7.46 | 72.03 5.88 7.27 | 71.87 5.90 7.24 |
| XR1877 | $C_{18}H_{15}N_3O_4S$ 369 | 370 100% 387 86% DCI $NH_3$ | CDCl$_3$ 2.85(3H, s), 3.19(3H, s), 7.06–7.13(2H, m), 7.32(1H, s), 7.35(2H, d), 7.41(1H, s), 7.47(1H, m), 7.53(1H, t), 7.66(1H, t), 8.16(1H, d). | | | |
| XR1799 | $C_{22}H_{19}N_3O_2$ | 309 MH$^+$ (100%) CI $NH_3$ | CDCl$_3$ 7.47(1H, s), 7.32–7.18(5H, m), 7.13(1H, s), 6.93(1H, s), 6.52(1H, d), 6.43(1H, q), 3.22(3H, s), 2.88(3H, s). | | | |
| XR1800 | $C_{27}H_{27}N_3O_4$ | 458 MH$^+$ (100%) CI $NH_3$ | CDCl$_3$ 8.16(1H, d), 7.62(1H, s), 7.58(1H, d), 7.42–7.23(9H, m), 3.07(3H, s), 3.0(3H, s), 1.69(9H, s). | C H N | 70.88 5.95 9.18 | 70.74 6.05 9.05 | 70.67 6.02 8.99 |

-continued

| No. | Mol. Formula (M. Wt) | Mass spec m/z, mass intensity (mode) | $^1$H nmr Solvent δ all 400 MHz | Microanalysis | | |
|---|---|---|---|---|---|---|
| | | | | | Calc | Found |
| XR1880 | $C_{25}H_{22}N_2O_4$ 414 | 415 100% DCI NH$_3$ | CDCl$_3$ 2.94(3H, s), 3.82(3H, s), 4.93(2H, s), 6.57(1H, s), 6.89(2H, d), 7.02(1H, s), 7.09(2H, m), 7.12(1H, s), 7.21–7.28 (overlapping sample & solvent), 7.53(1H, s), 7.66(1H, s). | | | |
| XR1777 | $C_{23}H_{22}N_2O_3$ 374 | MH+ (100%) 375 376 (30%), 374 (30%). DCI NH$_3$ | CDCl$_3$ 7.48–6.88(13H, m), 3.85(3H, s), 3.52(3H, s), 3.00(3H, s). | C H N | 73.78 5.92 7.48 | 73.38 5.85 7.43 | 73.40 5.94 7.39 |
| XR1871 | $C_{20}H_{24}N_2O_2$ 324 | | CDCl$_3$ 7.40–7.26(5H, m), 7.15(1H, d), 6.05(1H, d), 3.37(3H, s), 2.89(3H, s), 2.48(1H, m), 1.85–1.70(5H, m), 1.35–1.22(5H, m). | C H N | 74.05 7.46 8.63 | 73.83 7.40 8.61 | 73.73 7.37 8.58 |
| XR1938 | $C_{24}H_{25}N_3O_2$ 387 | MH+ (100%) 388 CI NH$_3$ | CDCl$_3$ 7.52–7.22(7H, m), 7.18(1H, s), 6.90(1H, s), 6.85(2H, m), 6.68(2H, d), 3.50(3H, s), 3.00(6H, s), 2.92(3H, s). | | | |
| XR1932 | $C_{28}H_{24}N_2O_2$ 420 | MH+ (100%) 421 CI NH$_3$ | CDCl$_3$ 7.45–7.28(15H, m), 7.20(1H, s), 6.95(1H, d), 6.84(1H, d), 3.55(3H, s), 2.89(3H, s). | | | |
| XR1933 | $C_{19}H_{22}N_2O_2$ 310 | MH+ (100%) 311 CI NH$_3$ | CDCl$_3$ 8.06(1H, brs), 7.40–7.23(6H, m), 6.05(1H, d), 2.95(3H, s), 2.22(1H, m), 1.85–1.68(4H, m), 1.45–1.21(6H, m). | | | |
| 1935 | $C_{30}H_{25}N_3O_4$ = 491 | mH$^+$(45%)-492 Also (40%)-305, 188-(100%) CI/NH$_3$ | CDCl$_3$ 8.02(d, 2H), 7.57–7.50(m, 2H), 7.38–7.25(m, 7H), 7.22(d, 2H), 7.06(m, 1H), 6.91(d, 1H), 6.78(s, 1H), 4.56(t, 2H), 3.98(t, 2H), 2.95(s, 3H), 2.35(quintet, 2H) | | | |
| 1934 | $C_{26}H_{25}N_3O_4$ = 443 | mH$^+$(20%)-444 Also (100%)-140 CI/NH$_3$ | CDCl$_3$ 400mH$_2$ 8.05(d, 2H), 7.45–7.28(m, 9H), 6.92(s, 1H), 4.45(t, 2H), 3.76(t, 2H), 2.98(s, 3H), 2.68(s, 4H), 2.20(quintet, 2H). | C H N | 70.41 5.68 9.47 | 70.29 5.71 9.38 | 70.41 5.68 9.38 |
| 1932 | $C_{26}H_{25}N_3O_4$ = 443 | mH$^+$(100%)-444 | 7.41–7.32(m, 10H), | | | |

-continued

| No. | Mol. Formula (M. Wt) | Mass spec m/z, mass intensity (mode) | $^1$H nmr Solvent δ all 400 MHz | Microanalysis Calc | Found |
|---|---|---|---|---|---|
| | | Also 352(10%), 317(30%), 140(90%) CI/NH$_3$ | 7.22(s, 1H), 7.19(s, 1H), 3.60(t, 2H), 3.30(t, 2H), 3.02(s, 3H), 2.56(s, 4H), 1.72(quintet, 2H). | | |

We claim:

1. A compound selected from the group consisting of a diketopiperazine of formula (Aa):

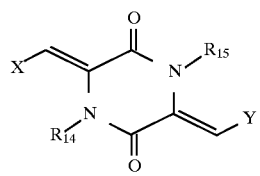

wherein
$R_{14}$ is H or $C_1$–$C_6$ alkyl optionally substituted by phenyl;
$R_{15}$ is H or $C_1$–$C_6$ alkyl optionally substituted by an N-phthalimidyl, N-succinimidyl or oxo or dioxo-indolinyl group; and
one of X and Y is a phenyl ring which is unsubstituted or substituted by one or more substituents selected from halogen, $C_1$–$C_6$ alkoxy, —NO$_2$ and $NR_{11}R_{12}$ wherein $R_{11}$ and $R_{12}$ are each, independently, H or $C_1$–$C_6$ alkyl; and the other is a heterocyclic ring selected from the group consisting of furan thiophene, pyridine and indole, the indole ring being optionally N-substituted by phthalimidyl-$C_1$–$C_6$-alkyl, succinimidyl-$C_1$–$C_6$-alkyl, oxo- or dioxo-indolenyl, —(CH$_2$)$_n$COOR$_{11}$ or —(CH$_2$)$_n$COOCH$_2$Ph wherein $R_{11}$ is H or $C_1$–$C_6$ alkyl and n is 0, 1 or 2, a cyclohexyl group or a group —CH=CHPh or —CH=C(Ph)$_2$; with the proviso that at least one of $R_{14}$ and $R_{15}$ is other than hydrogen; pharmaceutically acceptable salts thereof and pharmaceutically acceptable esters thereof selected from branched and unbranched, saturated and unsaturated $C_1$–$C_6$ alkyl esters.

2. A compound according to claim 1 wherein, when X or Y is a heterocyclic ring, it is selected from 4-pyridyl, furan-2-yl, furan-3-yl, thiophen-2-yl thiophen-3-yl and optionally N-substituted indol-3-yl groups.

3. A compound according to claim 1 selected from:
(3Z,6Z)-6-Benzylidene-1-methyl-3-(1-tert-butoxycarbonyl-3-indolyl)methylene-2,5-piperazinedione;
(3Z,6Z)-1-Benzyl-6-benzylidene-3-(4-pyridyl)methylene-2,5-piperazinedione;
(3Z,6Z)-1,4-Dimethyl-3-(1-tert-butoxycarbonyl-3 -indolyl)methylene-6-(2-thienylidene)-2,5-piperazinedione;
(3Z,6Z)-1-Benzyl-6-benzylidene-3-(4-pyridyl)methylene-2,5-piperazinedione;
(3Z,6Z)-3-Benzylidene-1,4-dimethyl-6-(1-tert-butoxycarbonyl-3-indolyl)methylene-2,5-piperazinedione;
(3Z,6Z)-3-Benzylidene- I ,4-dimethyl-6-[ i -(3-phthalimidopropyl)-3-indolyl]methylene-2 , 5-piperazinedione;
(3Z,6Z)-3-Benzylidene-6-(1-methoxycarbonyl-3-indolyl)methylene-1,4-dimethyl-2,5-pi perazinedione;
(3Z,6Z)-3-Benzylidene-6-(1-benzyloxycarbonyl-3-indolyl)methylene-1,4-dimethyl-2,5-piperazinedione;
(3Z,6Z)-3-Benzylidene-1,4-dimethyl-6-(γ-phenylcinnamylidene)-2,5-piperazinedione;
(3Z,6Z)-3-Benzylidene-1,4-dimethyl-6-(1-tert-butoxycarbonyl-3-indolyl)methylene-2,5-piperazinedione;
(3Z)-3-Benzylidene-1,4-dimethyl-6-(2-oxo-3-indolinylidene)-2,5-piperazinedione;
(3Z,6Z)-6-(3-furylmethylene)-3-(4-methoxybenzylidene-1-methyl-2,5-piperazinedione;
(3Z,6Z)-3-Benzylidene-6-(4-dimethylaminocinnamylidene)-1,4-dimethyl-2,5-piperazinedione;
(3Z,6Z)-6-Benzylidene-3-cyclohexylmethylene-1-methyl-2,5 -piperazinedione;
(3Z,6Z)-3-Benzylidene-6-(2-furyl)methylene- 1,4-dimethyl-2,5-piperazinedione;
(3Z,6Z)-3-Benzylidene-6-(3-indolyl)methylene- 1,4-dimethyl-2,5-piperazinedione;
(3Z,6Z)-3-(4-Methoxybenzylidene)-1-methyl-6-(2-thienylmethylene)-2,5-piperazinedione;
(3Z,6Z)-3-Benzylidene-1-methyl-6-(3-thienylmethylene)-2,5-piperazinedione;
(3Z)-3-Benzylidene-1,4-dimethyl-6-(1-methyl-2-oxo-3-indolinylidene)-2,5-piperazinedione;
(3Z,6Z)-6-(4-Methoxybenzylidene)-1-methyl-3-(1-tert-butoxycarbonyl-3-indolyl)methylene-2,5-piperazinedione;
(3Z,6Z)-3-Cinnamylidene-6-(4-methoxybenzylidene)-1,4-dimethyl-2,5-piperazinedione;
(3Z,6Z)-6-Benzylidene-3-(2-furylidene)-1,4-dimethyl-2,5-piperazinedione;
(3Z,6Z)-3-Benzylidene-6-cyclohexylmethylene-1,4-dimethyl-2,5-piperazinedione;
(3Z,6Z)-6-(2,6-dichlorobenzylidene)-3-(1-tertbutoxycarbonyl-3-indolyl)methylene-1,4-dimethyl-2,5-piperazinedione;
(3Z,6Z)-4-benzyl-3-(1-tertbutoxycarbonyl-3-indolyl)methylene-6-(4-methoxybenzylidene)-1-methyl-2,5-piperazinedione;
(3Z,6Z)-6-(3-furylmethylene)-6-(1-tertbutoxycarbonyl-3-indolyl)methylene-1,4-dimethyl-2,5-piperazinedione;
(3Z,6Z)-1,4-dimethyl-6-(2-nitrobenzylidene)-3-(2-thienylmethylene)-2,5-piperazinedione;
(3Z,6Z)-4-Benzyl-3-(3-furylmethylene)-6-(4-methoxybenzylidene)-1-methyl-2,5-piperazinedione;
(3Z,6Z)-3-(3-Furylmethylene)-6-(4-methoxybenzylidene)-1-methyl-2,5-piperazinedione;
(3Z,6Z)-6-(4-Methoxybenzylidene)-1-methyl-3-(2-thienylmethylene)-2,5-piperazinedione;
(3Z,6Z)-3-Benzylidene-1-methyl-6-(2-thienylmethylene)-2,5-piperazinedione, and the pharmaceutically acceptable salts thereof.

4. A pharmaceutical or veterinary composition comprising a pharmaceutically or veterinarily acceptable carrier or diluent and, as an active principle, a compound as claimed in claim 1.

5. A method of treating resistance to an anthracycline antibiotic which has antineoplastic activity in a patient harbouring a tumour, which method comprises administering to a patient in need thereof a therapeutically effective amount of a compound as defined in claim 1.

6. A method according to claim 5 wherein the anthracycline antibiotic is doxorubicin or daunorubicin.

7. A method according to claim 5 which comprises administering the said compound to the patient while the tumour is exposed to the said anthracycline antibiotic.

8. A process for preparing a compound as defined in claim 1, the process comprising:

(a) condensing a compound of formula (I):

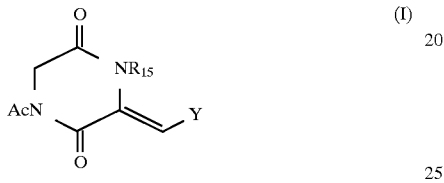

wherein $R_{15}$ and Y are as defined in claim 1 and are optionally protected, with a compound of formula (II):

wherein X is as defined in claim 1 and is optionally protected, in the presence of a base in an organic solvent thereby obtaining a compound of formula Aa in which $R_{14}$ is hydrogen; or (b) condensing a compound of formula (I'):

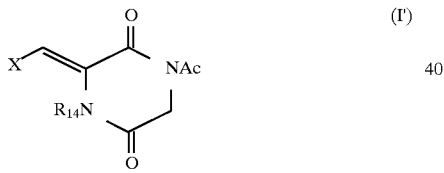

wherein $R_{14}$ and X are as defined in claim 1 and are optionally protected with a compound of formula (III):

wherein Y is as defined in claim 1 and is optionally protected, in the presence of a base in an organic solvent; and (c) if desired, converting the resulting compound of formula Aa in which $R_{14}$ or $R_{15}$, respectively, is hydrogen into a corresponding compound of formula Aa in which $R_{14}$, $R_{15}$, respectively, is a $C_1-C_6$ alkyl group, by treatment with an alkylating agent of formula $R_{14}$—X or $R_{15}$—X wherein $R_{14}$ and $R_{15}$ are as defined in claim 1 and X is a halogen; and/or, if required, removing optionally present protecting groups, or, if desired, converting a compound of formula Aa in which $R_{15}$ is hydrogen into a compound of formula Aa wherein $R_{16}$ is $C_1-C_6$ alkyl optionally substituted as defined in claim 1, by treatment with an alkylating agent of formula $R_{16}$—X wherein $R_{16}$ is as defined in claim 1 and X is a halogen; and/or if required, removing optionally present protecting group, if desired, converting a compound of formula Aa into a pharmaceutically acceptable salt or ester thereof, and/or, if desired, converting a salt or ester into a free compound.

9. A compound selected from the group consisting of a diketopiperazine of formula (Ab):

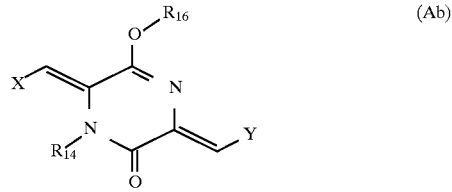

wherein $R_{14}$ is H or $C_1-C_6$ alkyl optionally substituted by phenyl;

$R_{16}$ is $C_1-C_6$ alkyl optionally substituted by an N-phthalimidyl, N-succinimidyl or oxo- or dioxoindolinyl group;

X and Y, which may be the same or different, are independently selected from (i) a heterocyclic ring selected from furan, thiophen, pyridine and indole, the indole ring being optionally N-substituted by phthalimidyl-$C_1-C_6$-alkyl, succinimidyl-$C_1-C_6$-alkyl, oxo- or dioxo-indolinyl, —$(CH_2)_n COOR_{11}$ or —$(CH_2)_n COOCH_2Ph$, wherein $R_{11}$ is H or $C_1-C_6$ alkyl and n is 0, 1 or 2;

(ii) a phenyl ring which is unsubstituted or substituted by one or more substituents selected from halogen, $C_1-C_6$ alkoxy, —$NO_2$ and $NR_{11}R_{12}$ wherein $R_{11}$ and $R_{12}$ are each, independently, H or $C_1-C_6$ alkyl;

(iii) a cyclohexyl group; and (iv) a group —CH=C($R_{17}$Ar);

$R_{17}$ is H or optionally substituted phenyl and Ar is optionally substituted phenyl, the optional substituent on the phenyl ring in each case being selected from halogen, —$NO_2$, —$N(R_{11}R_{12})$ wherein $R_{11}$ and $R_{12}$ are as defined above and $C_1-C_6$ alkoxy;

pharmaceutically acceptable salts thereof and pharmaceutically acceptable esters thereof selected from branched and unbranched, saturated and unsaturated $C_1-C_6$ alkyl esters;

with the proviso that X and Y are not both a phenyl ring as defined above under (ii).

10. A compound according to claim 9 wherein one of X and Y is an unsubstituted or substituted phenyl ring and the other is a heterocyclic ring, a cyclohexyl group or a group —CH=CHPh or —CH=C(Ph)$_2$.

11. A compound according to claim 9 wherein, when X or Y is a heterocyclic ring, it is selected from 4-pyridyl, furan-2-yl, furan-3-yl, thiophen-2-yl, thiophen-3-yl and optionally N-substituted indol-3-yl groups.

12. A compound according to claim 9 which is selected from the group consisting of:

(3Z,6Z)-6-Benzylidene-1-methyl-5-(3-phthalimidopropoxy)-3-(1-tert-butoxycarbonyl-3-indolyl)methylene-3,6-dihydro-2-pyrazinone; and (3Z,6Z)-6-Benzylidene-5-methoxy-3-(2-thienylidene)-3,6-dihydro-2(1H)-pyrazinone; and the pharmaceutically acceptable salts thereof.

13. A pharmaceutical or veterinary composition comprising a pharmaceutically or veterinarily acceptable carrier or diluent and, as an active principle, a compound as claimed in claim 9.

14. A method of treating resistance to an anthracycline antibiotic which has antineoplastic activity in a patient harbouring a tumour, which method comprises administering to a patient in need thereof a therapeutically effective amount of a compound as defined in claim 9.

15. A method according to claim 14 wherein the anthracycline antibiotic is doxorubicin or daunorubicin.

16. A method according to claim 14 which comprises administering the said compound to the patient while the tumour is exposed to the said anthracycline antibiotic.

* * * * *